United States Patent
Li et al.

(10) Patent No.: US 7,543,507 B2
(45) Date of Patent: Jun. 9, 2009

(54) FAILURE ANALYSIS SYSTEM FOR PRINTED CIRCUIT BOARD AND METHOD USING THE SAME

(75) Inventors: Lei Li, Shenzhen (CN); Ping Chen, Shenzhen (CN); Zhi Cheng, Shenzhen (CN); Hu Li, Shenzhen (CN); Dong Li, Shenzhen (CN); Yong-Zhi Tao, Shenzhen (CN); Lin-Sen Dong, Shenzhen (CN)

(73) Assignees: Shenzhen Futaihong Precision Industry Co., Ltd., ShenZhen, Guangdong Province (CN); FIH (Hong Kong) Limited, Kowloon (HK)

( * ) Notice: Subject to any disclaimer, the term of this patent is extended or adjusted under 35 U.S.C. 154(b) by 0 days.

(21) Appl. No.: 11/862,484

(22) Filed: Sep. 27, 2007

(65) Prior Publication Data
US 2008/0210015 A1 Sep. 4, 2008

(30) Foreign Application Priority Data
Feb. 2, 2007 (CN) .................. 2007 1 0073072

(51) Int. Cl.
*G01N 3/20* (2006.01)
(52) U.S. Cl. ........................ 73/851; 324/763
(58) Field of Classification Search .............. 73/851, 73/81–85, 87, 852, 781; 324/763, 71.1
See application file for complete search history.

(56) References Cited

U.S. PATENT DOCUMENTS 2,670,624 A * 3/1954 Faris, Jr. et al. ............... 73/851
5,184,517 A * 2/1993 Kelzer ........................... 73/851
5,199,305 A * 4/1993 Smith et al. .................... 73/851
5,231,882 A * 8/1993 Bertele et al. .................. 73/852
5,567,884 A * 10/1996 Dickinson et al. ............. 73/814
2005/0093552 A1* 5/2005 Ahrikencheikh ............. 73/760

FOREIGN PATENT DOCUMENTS

| JP | 56014905 A | * | 2/1981 |
| JP | 2000284248 A | * | 10/2000 |
| JP | 2003065920 A | * | 3/2003 |
| SU | 1723679 | * | 3/1992 |
| WO | WO 2004099803 A1 | * | 11/2004 |

OTHER PUBLICATIONS

K. Jonnalagadda, "Reliability of via-in-pad structure in mechanical cycling fatigue." Microelectronics Reliability 42 (2002) pp. 253-258.*
Rusek, Andrew. "Oscilloscope." Wiley Encyclopedia of Electrical and Electronics Engineering. Published in 1999.*

* cited by examiner

*Primary Examiner*—Harshad Patel
*Assistant Examiner*—Punam Patel
(74) *Attorney, Agent, or Firm*—Steven M. Reiss

(57) ABSTRACT

A failure analysis system (900) for printed circuit board (600) includes testing equipment (100) and a monitor (200). The testing equipment includes a base (120), a fixing body (180), a supporting arm (140) and a micrometer (160). The fixing body and the supporting arm are both firmly fixed on the base. The printed circuit board is fastened to the fixing body. The micrometer is slidingly attached to the supporting arm. The micrometer has a pin (1612) at one end thereof for resisting one end of the printed circuit board. The monitor electronically connects with the printed board for receiving signals from the printed circuit board. When the pin of the micrometer reaches a certain position, the signal transmitted to the monitor is broken.

8 Claims, 3 Drawing Sheets

FAILURE ANALYSIS SYSTEM FOR PRINTED CIRCUIT BOARD AND METHOD USING THE SAME

BACKGROUND OF THE INVENTION

1. Field of the Invention

The present invention relates to failure analysis systems and methods using the same, particularly, to a failure analysis system used to test a critical curve angle of a printed circuit board and a method using the same.

2. Description of Related Art

Most of printed circuit boards often need to be fixed in a given main body using screws. During assembly, the printed circuit board can easily be tightly locked so as to cause the printed circuit board to become bent. When the printed circuit board bends past a certain angle, wires or electronic elements in the printed circuit board can become damaged. This will affect the quality of the products. Thus, it is necessary to analyze and test the maximal allowable value of bending deformation of the printed circuit board so as to avoid failure of printed circuit boards.

A conventional projector testing system or a three-dimensional testing apparatus is often used to do failure analysis on printed circuit boards. However, the volume of the projector testing system or the three-dimensional testing apparatus is enormous, making it difficult to move. In addition, the structure of the projector testing system or the three-dimensional testing apparatus is complicated, and the test cost is very high.

Therefore, a new failure analysis system for printed circuit board is desired in order to overcome the above-described problems.

SUMMARY OF THE INVENTION

In one embodiment thereof, a failure analysis system for printed circuit board includes testing equipment and a monitor. The testing equipment includes a base, a fixing body, a supporting arm and a micrometer. The fixing body and the supporting arm are both firmly fixed on the base. The printed circuit board is fastened to the fixing body. The micrometer is slidingly attached to the supporting arm. The micrometer has a pin at one end thereof for resisting one end of the printed circuit board. The monitor electronically connects with the printed board for receiving signal from the printed circuit board. When the pin of the micrometer reaches an angle at which the circuit board being tested breaks then the signal transmitted to the monitor should be broken.

Other advantages and novel features will become more apparent from the following detailed description when taken in conjunction with the accompanying drawings.

BRIEF DESCRIPTION OF THE DRAWINGS

Many aspects of the failure analysis system can be better understood with reference to the following drawings. The components in the drawings are not necessarily drawn to scale, the emphasis instead being placed upon clearly illustrating the principles of the present failure analysis system. Moreover, in the drawings, like reference numerals designate corresponding parts throughout the several views.

DETAILED DESCRIPTION OF THE INVENTION

Figure 1:
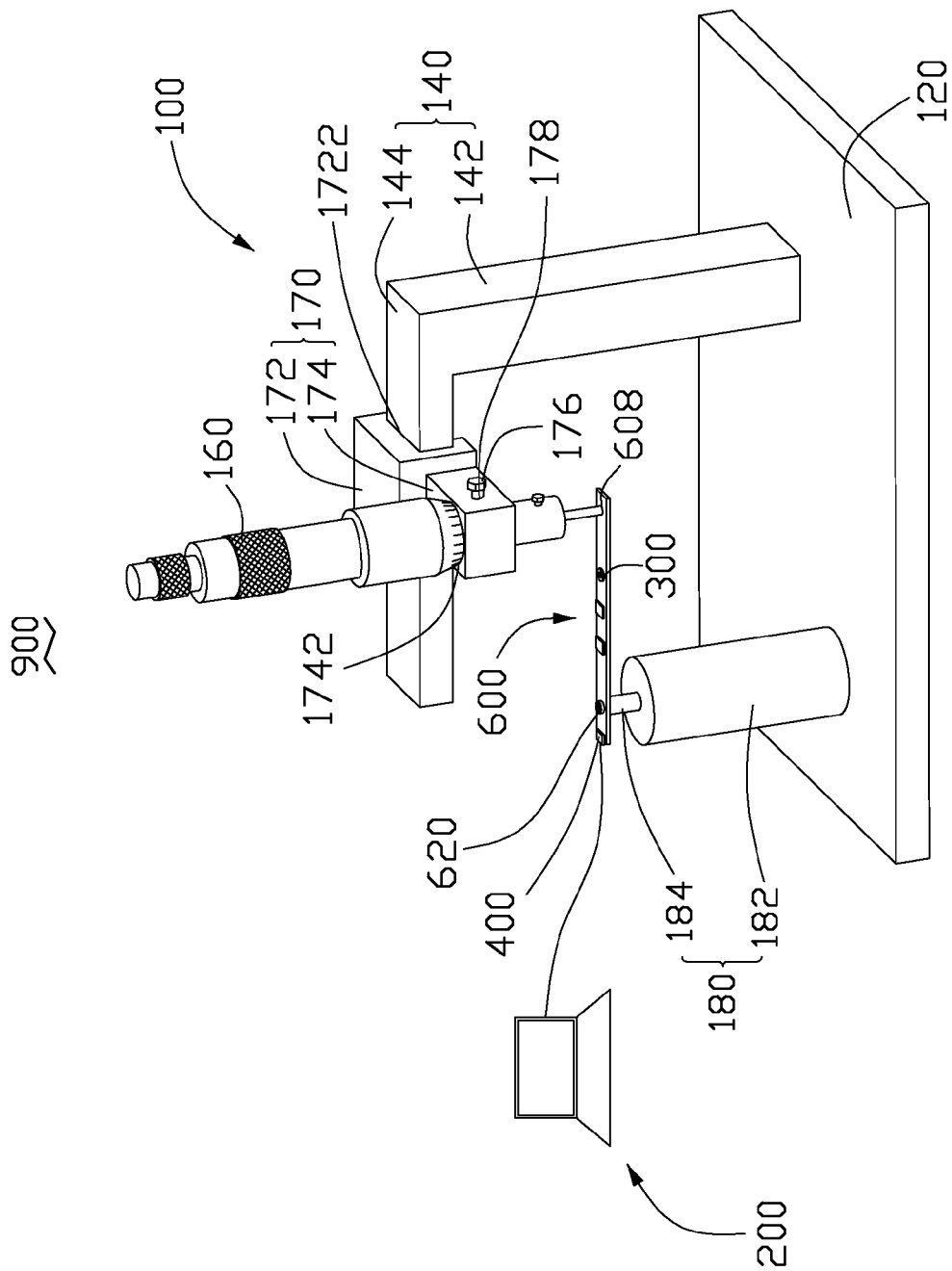
FIG. 1 is an isometric view of a failure analysis system, in accordance with a present embodiment, showing a printed circuit board and a spiral micrometer.

Referring now to FIG. 1, a failure analysis system 900 is used to test a critical curve angle of a printed circuit board 600. The failure analysis system 900 includes a testing equipment 100, a monitor 200, a camera 300 and an output element 400, in accordance with a present embodiment. The camera 300 and the output element 400 are fixed on the printed circuit board 600. The monitor 200 electronically connects with the printed circuit board 600.

The testing equipment 100 has a base 120, a supporting arm 140, a spiral micrometer 160, a sliding member 170 and a fixing body 180. The base 120 is a rectangular flat board. The supporting arm 140 is L-shaped and has a vertical portion 142 and a horizontal portion 144. The horizontal portion 144 vertically extends from one end of the vertical portion 142, and the other end of the vertical portion 142 is perpendicularly fixed on one side of the base 120. The horizontal portion 144 and the vertical portion 142 both have a rectangular cross section in longitudinal direction thereof. A cross sectional area of the vertical portion 142 is larger than that of the horizontal portion 144, so that the vertical portion 142 can stably support the horizontal portion 144.

The sliding member 170 has a sliding portion 172 and a holding portion 174. The sliding portion 172 is approximately rectangular and has a sliding slot 1722 defined in a middle area thereof. The sliding slot 1722 is configured for receiving the horizontal portion 144 of the supporting arm 140, so that the sliding portion 172 can slide along the horizontal portion 144. The holding portion 174 horizontally extends from the sliding portion 172 and has a receiving hole 1742 defined therein. The extending direction of the receiving hole 1742 is perpendicular to the extending direction of the sliding slot 1722. A screw hole 178 is defined in the holding portion 174 and extends to the receiving hole 1742.

The fixing body 180 includes a column 182 and a positioning post 184. The column 182 is vertically fixed on the base 120. The positioning post 184 is positioned at a central area of an end surface of the column 182. A diameter of the positioning post 184 is much smaller than that of the column 182. The positioning post 184 has a screw 620 fixed at an end thereof. It should be understood that the fixing body 180 can be a clamping mechanism configured for clamping one end of the printed circuit board 600.

Figure 2:
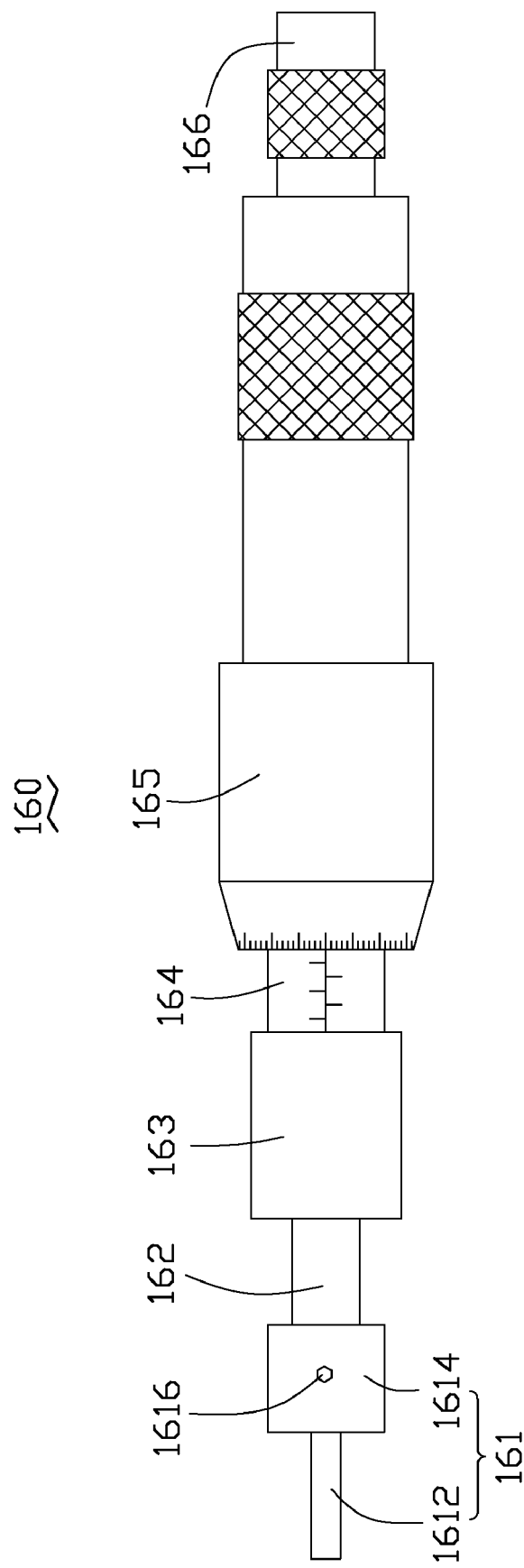
FIG. 2 is a front view of the spiral micrometer shown in FIG. 1.

Also referring to FIG. 2, the micrometer 160 includes a resisting portion 161, a sliding pole 162, a fixing portion 163, a scale sleeve 164, a scale rotating sleeve 165 and an adjusting portion 166. The resisting portion 161 has a pin 1612 at one end thereof and a circular block 1614 integrally formed with the pin 1612. The block 1614 has a groove configured (i.e., structured and arranged) for receiving the sliding pole 162. The resisting portion 161 is firmly fastened to the sliding pole 162 by screws 1616. The sliding pole 162 is slidingly received in the fixing portion 163 and connects with the adjusting portion 166. The scale rotating sleeve 165 covers the scale sleeve 164 and connects with the adjusting portion 166. The sliding pole 162 and the resisting portion 161 can move forward or backward by rotating the adjusting portion 166 or the scale rotating sleeve 165.

The monitor 200 is used to determine whether the printed circuit board 600 has failed. The monitor 200 electronically connects with the printed circuit board 600 and can receive signals from the printed circuit board 600. The monitor 200 is a computer in this embodiment. The computer can show the signal transmitted from the printed circuit board 600 in a display thereof.

The printed circuit board 600 is fixed on the positioning post 184 by the screw 620 at one end thereof. A circular recess 608 is defined in the other end of the printed circuit board 600. The diameter of the recess 608 is larger than the diameter of the pin 1612 of the micrometer 160, so as to receive one end of the pin 1612.

The camera 300 and the output element 400 are mounted on the printed circuit board 600 and electronically connect with the monitor 200. The monitor 200 supplies electric energy to the camera 300 and controls the camera 300 to take photos of a predetermined area of the printed circuit board 600. The camera 300 is electronically connected with the output element 400, so that the output element 400 can transmit the information of the photos to the monitor 200.

In assembly, a free end of the horizontal portion 144 of the supporting arm 140 passes the sliding slot 1722 of the sliding member 170, so that the sliding member 170 can slide along the horizontal portion 144. The micrometer 160 is inserted into the receiving hole 1742 of the sliding member 170 via a top-down direction, with the resisting portion 161 extending through the receiving hole 1742 and located below the receiving hole 1742. The sleeve 164 of the micrometer 160 is received in the receiving hole 1742 and may be locked by a screw 176 received in the screw hole 178, so that the micrometer 160 is firmly fastened to the sliding member 170 once the screw 176 is manually driven to lock the sleeve 164. The printed circuit board 600 is fixed on the positioning post 184 by the screw 620.

Figure 3:
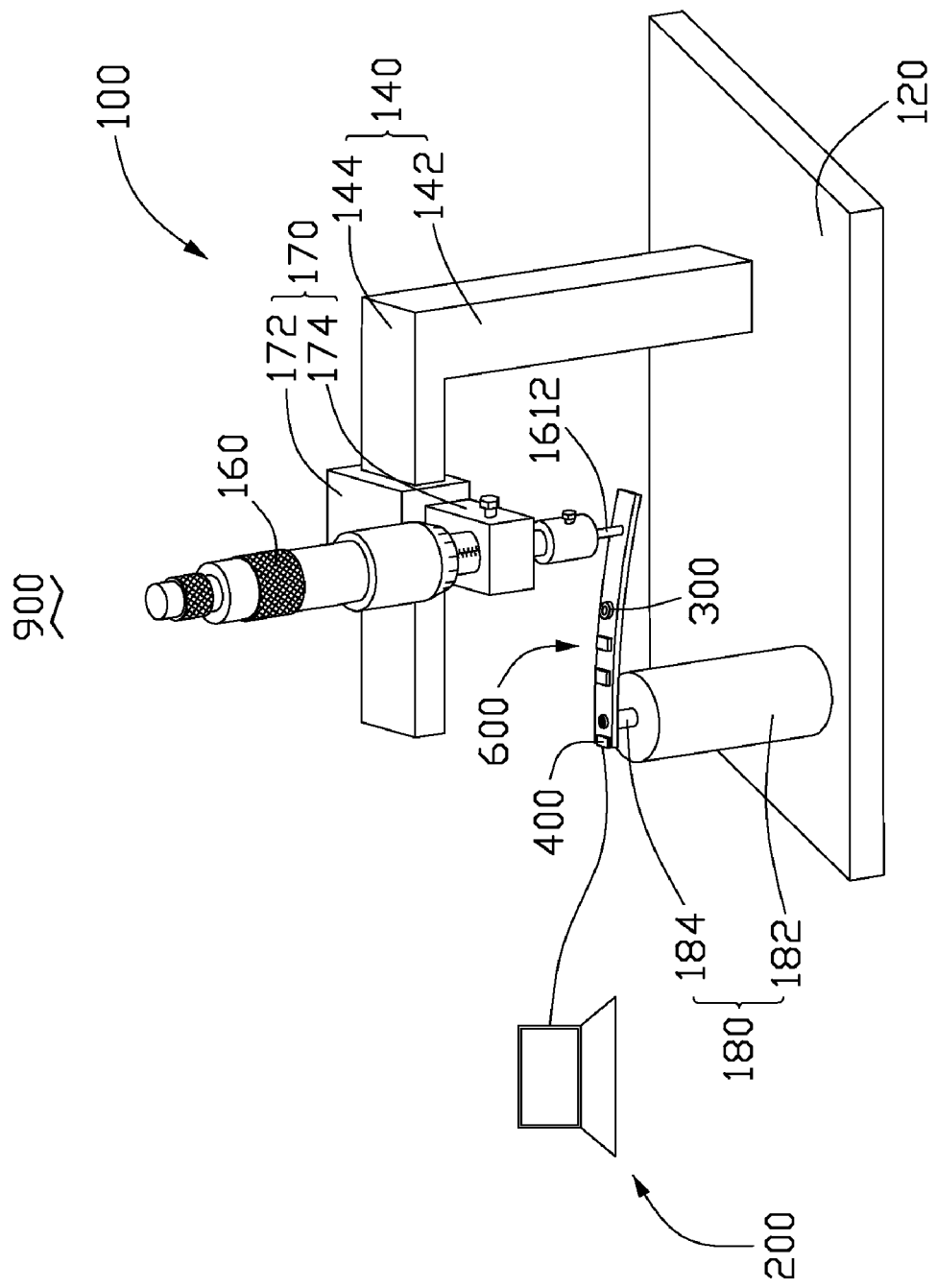
FIG. 3 is similar to FIG. 1, but showing the printed circuit board during a test.

In use, referring to FIG. 3, firstly, the sliding member 170 slides along the horizontal portion 144 until the pin 1612 of the micrometer 160 is positioned to be locked in the blind recess 608 of the printed circuit board 600. The adjusting portion 166 is rotated until the pin 1612 touches the printed circuit board 600. It has been set up in advance so that the printed circuit board 600 will be powered on and the camera 300 thereon automatically take photos once the monitor 200 is electrically connected to the printed circuit board 600. The camera 300 takes photos of a predetermined area of the printed circuit board and the output element 400 transmits the signal of the photos to the monitor 200 when the monitor is electrically connected to the printed circuit board 60. It should be understood that if the printed circuit board 600 fails, the signal of the photo taken by the camera 300 cannot be transmitted to the output element 400, and the monitor 200 cannot receive the photos. This means if the signal disappears, the printed circuit board 600 has failed. Before the test is slatted, the user reads and writes down the original value of the micrometer 160. The adjusting portion 166 of the micrometer 160 is slowly rotated downwards, The pin 1612 resists the free end of the printed circuit board 600 and the printed circuit board 600 is bent. When the printed circuit board 600 bends beyond a certain angle, the printed circuit board 600 fails and the monitor 200 receives no signal from the printed circuit board 600. At this moment, the adjusting portion 166 stops rotating, and the user can read and write down the final number on the micrometer 160. The original value of the micrometer 160 is subtracted from the final number of the micrometer 160 by the user to determine a result. i.e., a critical displacement value of the pin 1612 in length units. The user compares the result to a predetermined angle check list, to determine a critical curve angle of the printed circuit board 600.

In an alterative embodiment, the camera 300 and the output element 400 may be omitted, and the computer can be replaced by an oscillograph (or an oscilloscope). The oscillograph electronically connects with the printed circuit board 600 and shows a various graph of the signal. When the curve is abnormal or disappears from the oscillograph, that means the printed circuit board 600 has failed.

It should be understood that the test using the failure analysis system 900 for printed circuit board 600 simulates the printed circuit board 600 being bent during assembling. It is easily to do the test so as to gain the critical curve angle of the printed circuit board 600.

It is to be further understood that even though numerous characteristics and advantages of the present embodiments have been set forth in the foregoing description, together with details of the structures and functions of the embodiments, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A failure analysis system for a printed circuit board, comprising:
   a testing equipment including:
      a base;
      a fixing body for fastening a printed circuit board thereon;
      a supporting arm being fixed on the base; and
      a micrometer being slidingly attached to the supporting arm, the micrometer including a pin at one end thereof, the pin being operative to displace and bend the printed circuit board from a rest position until the printed circuit board fails, the micrometer configured for measuring the displacement of the printed circuit board when it fails to determine a critical displacement value of the pin in length units; and
   a monitor being electronically connecting with the printed circuit board for detecting signals sent from the printed circuit board and determining whether the printed circuit board has failed;
   a camera; and
   an output element, wherein the camera and the output element being mounted on the printed circuit board, the camera electronically connecting with the output element, and the monitor electronically connecting with the output element.

2. The failure analysis system as claimed in claim 1, further comprising a sliding member, wherein the sliding member defines a sliding slot, the sliding slot is configured for receiving the supporting arm, and the micrometer is fixed in the sliding member, the supporting arm comprises a horizontal portion and a vertical portion, the vertical portion being attached to the base, and the sliding member is slidably attached to the horizontal portion.

3. The failure analysis system as claimed in claim 2, wherein the supporting arm is L-shaped, and the horizontal portion is oriented perpendicular to the vertical portion.

4. The failure analysis system as claimed in claim 2, wherein the sliding member comprises a sliding portion and a fixing portion, the sliding slot is positioned in the sliding portion, and the fixing portion has a receiving hole for receiving the micrometer.

5. The failure analysis system as claimed in claim 1, wherein the micrometer is attached to the sliding member by screws.

6. The failure analysis system as claimed in claim 1, wherein the fixing body comprises a column and a positioning post, and the printed circuit board is fastened to the positioning post.

7. The failure analysis system as claimed in claim 1, wherein the monitor can be selected from the group consisting of a computer, an oscillograph and an oscilloscope.

8. A method for analyzing failure of a printed circuit board, comprising the steps of:

fixing an end of the printed circuit board to a fixing body, leaving other portions of the printed circuit suspended;

electronically connecting the printed circuit board to a monitor which supplies power to the printed circuit board thus for enabling the printed circuit board to continuously send signals, and the signals are detected by the monitor;

moving a micrometer pin to touch a second end of the printed circuit board;

recording a first value of the micrometer once the pin has just touched the printed circuit board;

further moving the micrometer bend the printed circuit board until the monitor detects no signals sent from the printed circuit board, simultaneously recording a second value of the micrometer;

calculating the distance of the pin moved according to the recorded first value and second value of the micrometer thereby determining a critical curve angle of the printed circuit board.

* * * * *